US011517453B2

(12) United States Patent
Guillemot et al.

(10) Patent No.: US 11,517,453 B2
(45) Date of Patent: Dec. 6, 2022

(54) BIOPRINTING PROCESS

(71) Applicant: Poietis, Pessac (FR)

(72) Inventors: Fabien Guillemot, Preignac (FR);
Bertrand Viellerobe, Merignac (FR);
Guillaume Simon, Merignac (FR);
Guillaume Vandeneeckhoutte,
Merignac (FR)

(73) Assignee: Poietis, Pessac (FR)

( * ) Notice: Subject to any disclaimer, the term of this patent is extended or adjusted under 35 U.S.C. 154(b) by 618 days.

(21) Appl. No.: 16/494,693

(22) PCT Filed: Mar. 8, 2018

(86) PCT No.: PCT/FR2018/050534
§ 371 (c)(1),
(2) Date: Sep. 16, 2019

(87) PCT Pub. No.: WO2018/167401
PCT Pub. Date: Sep. 20, 2018

(65) Prior Publication Data
US 2020/0046520 A1 Feb. 13, 2020

(30) Foreign Application Priority Data
Mar. 15, 2017 (FR) ..................... 1752130

(51) Int. Cl.
*A61F 2/50* (2006.01)
*C12M 3/00* (2006.01)
(Continued)

(52) U.S. Cl.
CPC ............ *A61F 2/5044* (2013.01); *A61F 2/105* (2013.01); *A61F 2/50* (2013.01); *C12M 3/00* (2013.01);
(Continued)

(58) Field of Classification Search
CPC ......... A61F 2/105; A61F 2/5044; C12M 3/00; C12M 21/08; B33Y 10/00; B33Y 30/00; B33Y 50/02; B33Y 70/00; B33Y 80/00
See application file for complete search history.

(56) References Cited

U.S. PATENT DOCUMENTS

| 5,432,718 A | 7/1995 | Molvig et al. |
| 7,000,093 B2 | 2/2006 | Mates |

(Continued)

FOREIGN PATENT DOCUMENTS

| WO | 2005/081970 A3 | 9/2005 |
| WO | 2011/107599 A1 | 9/2011 |

(Continued)

OTHER PUBLICATIONS

Ballet et al., A Multi-Agent Approach for Cellular Biology Simulation, The discreet and continuous life, (Sep. 2013), pp. 155-194.
(Continued)

*Primary Examiner* — Anh T Vo
(74) *Attorney, Agent, or Firm* — TraskBritt

(57) ABSTRACT

A bio-printing process comprises a step of preparing a target digital model representative of the three-dimensional organization of the tissue to be produced, a step of controlling a bio-printing instrument for the deposition of a plurality of layers of living cells and of biomaterials, a step of calculation of a digital printing model as a function of the digital model of the product to be produced, and of a model predicting change, and also characteristics of the constituents to be printed. The step of controlling the bio-printing instrument is carried out according to the digital printing model calculated in this way. A system is also described for implementing this process.

21 Claims, 4 Drawing Sheets

(51) Int. Cl.
*A61F 2/10* (2006.01)
*B33Y 10/00* (2015.01)
*B33Y 30/00* (2015.01)
*B33Y 50/02* (2015.01)
*B33Y 70/00* (2020.01)
*B33Y 80/00* (2015.01)

(52) U.S. Cl.
CPC .............. *C12M 21/08* (2013.01); *B33Y 10/00* (2014.12); *B33Y 30/00* (2014.12); *B33Y 50/02* (2014.12); *B33Y 70/00* (2014.12); *B33Y 80/00* (2014.12)

(56) References Cited

U.S. PATENT DOCUMENTS

2004/0084164 A1* 5/2004 Shannon ................ D21H 21/22
162/168.3
2008/0070304 A1* 3/2008 Forgacs ................ C12M 33/12
435/395

FOREIGN PATENT DOCUMENTS

| WO | 2013/158508 A1 | 10/2013 |
| WO | 2015/148646 A1 | 10/2015 |
| WO | 2016/097619 A1 | 6/2016 |

OTHER PUBLICATIONS

Barron et al., Laser Printing: A Novel Technique for Creating Heterogeneous 3-Dimensional Cell Patterns, Biomed Micro Devices, vol. 6, No. 2, (Jun. 2004), pp. 139-147 (abstract only).

Dababneh et al., Bioprinting Technology: A Current State-of-the-Art Review, J. Manuf. Sci. Eng., vol. 136, No. 6, (Dec. 2014), abstract only.

Griffith et al., Tissue Engineering-Current Challenges and Expanding Opportunities, Science, vol. 295, No. 5557, (Feb. 8, 2002), pp. 1009-1014, (abstract only).

Guillemot et al., High-Throughput Laser Printing of Cells and Biomaterials for Tissue Engineering, Acta Biomater, vol. 6, No. 7, (Jul. 2010), pp. 2494-2500 (abstract only).

International Search Report for International Application No. PCT/FR2018/050534 dated May 29, 2018, 3 pages.

International Written Opinion for International Application No. PCT/FR2018/050534 dated May 29, 2018, 5 pages.

Klebe et al., Cytoscription: Computer Controlled Micropositioning of Cell Adhesion Proteins and Cells, Journal of Tissue Culture Methods, vol. 16, Issue 3-4, (Sep. 1994), pp. 189-192, (abstract only).

Klebe, RJ, Cytoscribing: A Method for Micropositioning Cells and the Construction of Two- and Three-Dimensional Synthetic Tissues, Exp. Cell Res., vol. 179, No. 2, Dec. 1988), pp. 362-373, (abstract only).

Picault, Sebastien, De la Simulation Multi-Agents a la Simulations Multi-Niveaux. Pour une Reification des Interactions, https://tel.archives-ouvertes.fr/tel-00968661, (Apr. 1, 2014), English abstract only.

Riester et al., Laser Tool for Single Cell Transfer, Journal of Laser Micro/Nanoengineering, vol. 9, No. 2, (2014), pp. 93-97.

* cited by examiner

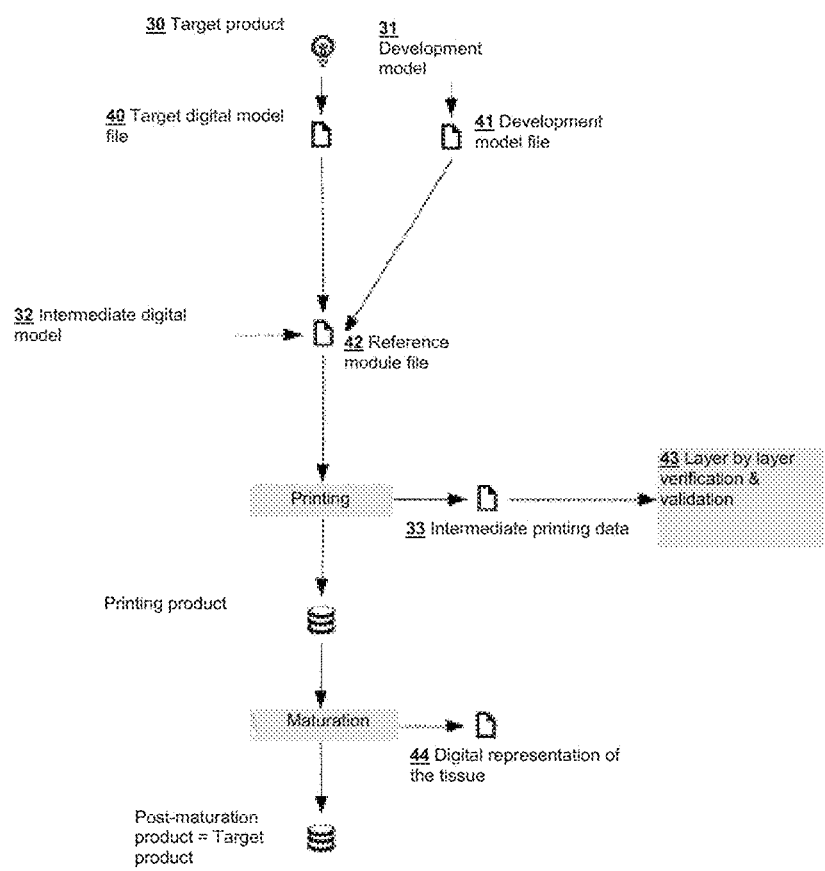

BIOPRINTING PROCESS

CROSS-REFERENCE TO RELATED APPLICATIONS

This application is a national phase entry under 35 U.S.C. § 371 of International Patent Application PCT/FR2018/050534, filed Mar. 8, 2018, designating the United States of America and published as International Patent Publication WO 2018/167401 A1 on Sep. 20, 2018, which claims the benefit under Article 8 of the Patent Cooperation Treaty to French Patent Application Serial No. 1752130, filed Mar. 15, 2017.

TECHNICAL FIELD

The present disclosure concerns the field of laser bio-printing by a computer-assisted transfer process for modelling and assembling living and optionally non-living materials with a prescribed 2D or 3D organization in order to produce bioengineered structures for use in regenerative medicine, pharmacology and cell biology studies.

BACKGROUND

Tissue engineering aims to design and develop biologically suitable alternatives to replace, restore or maintain the functions of native tissue or even an organ. An example is described in the article by Griffith, L. G., & Naughton, G. (2002), Tissue engineering—current challenges and expanding opportunities, Science, 295(5557), 1009-1014.

For these artificial (re)construction methods to be effective, they must reproduce as closely as possible the complexity of the target tissue, characterized and resulting from the action and counter-reaction loops exerted by the different tissue components (cells, extracellular matrix, morphogens) from the microscopic to the macroscopic scale. These interactions imply a close relationship between the shape or organization of tissues and their function. The fact is that traditional tissue engineering approaches have a number of limitations, in particular, the difficulty of controlling the complexity of tissues, their vascularization, the resulting customization and the safety of their production.

To overcome these limitations, the printing of biological elements, more commonly referred to as bio-printing, began to be imagined, as discussed in Klebe, R. (1988), Cytoscribing: A Method for Micropositioning Cells and the Construction of Two- and Three-Dimensional Synthetic Tissues, Experimental Cell Research, 179(2):362-373, and in Klebe, R., Thomas, C., Grant, G. Grant, A. and Gosh, P. (1994), Cytoscription: Computer controlled micropositioning of cell adhesion proteins and cells, Methods in Cell Science, 16(3): 189-192.

This technique allows organization of the different components of a biological tissue (living cells, biomaterials, molecules, etc.) while guaranteeing the maintenance of their post-printing properties, then assembling in 3D, layer by layer, these different components of the tissue. The major advantages of bio-printing over more traditional bio-manufacturing methods are reproducibility (automation), speed of execution (computer planning/parallelization) and the ability to customize.

There are now three key bio-printing technologies: ink-jet, bio-extrusion and laser-assisted printing (LAB) as outlined in Dabababneh, A. B., & Ozbolat, I. T. (2014), Bioprinting technology: a current state-of-the-art review, Journal of Manufacturing Science and Engineering, 136(6).

The state of the art is a solution known as "AFA-LIFT" and described in B. Hopp, T. Smausz, N. Kresz, N. Barna, Z. Bor, L. Kolozsvâri, D. B. Chrisey, A. Szabo, and A. Nôgrâdi, "Survival and proliferative ability of various living cell types after laser-induced forward transfer," Tissue Eng. 11, 1817-23 (2005).

The article J. A. Barron, P. Wu, H. D. Ladouceur, and B. R. Ringeisen, Biological laser printing: a novel technique for creating heterogeneous 3-dimensional cell patterns," Biomed, Microdevices 6, 139-147 (2004), also describes equipment of the "AFA LIFT or DRL-LIFT" type, where the laser direction is fixed, and the film supporting the cells to be transferred is mobile.

Another article, published in the Journal of laser micro/nanoengineering, Vol. 9, No 2-2014 under the title "Laser tool for single cell transfer," describes another example of process and equipment of the AFA-LIFT type.

The article F. Guillemot, A. Souquet, S. Catros, B. Guillotin, J. Lopez, M. Faucon, B. Pippenger, R. Bareille, M. Remy, S. Bellance, P. Chabassier, J. C. Fricain, and J. Amédée, High-throughput laser printing of cells and biomaterials for tissue engineering, Acta Biomater. 6, 2494-2500 (2010), describes an example of equipment to implement such a process.

In the state of the art, Patent Application Publication No. WO2016097619 is also known, which describes a method and equipment for printing with at least one ink, the method comprising a step of focusing a laser beam so as to generate a cavitation bubble in an ink film, a step of forming at least one ink droplet from a free surface of the ink film and a step of depositing the droplet onto a depositing surface of a receiving substrate, wherein the laser beam is oriented in the direction opposite to the gravitational force, the free surface of the film being oriented upwards toward the depositing surface placed over the ink film.

This configuration makes it possible, in particular, to obtain a substantially constant thickness for the ink film, while limiting the occurrence of settling phenomena, an also enables the use a wide range of inks.

Previously known solutions are not well adapted to the manufacture of tissues from living cells, which transform after the bio-printing step. Living cells deposited by transfer can adhere, proliferate, deform, move, differentiate, and/or enter into quiescence and apoptosis. As a result, the biological item produced by bio-printing is not fixed, and the tissue obtained after a maturation phase does not necessarily correspond to the tissue that was produced.

The previously known solutions do not allow construction of a predetermined model when the components of the tissue transform over time (4D printing) under the action of its own components or under the action of external (exogenous) stimuli such as temperature, pH, oxygen or $CO_2$ levels, etc.

BRIEF SUMMARY

The present disclosure concerns, in its most general sense, a bio-printing method comprising:
 a step of preparing a digital target model representative of the three-dimensional organization of the tissue to be manufactured, (also called a CAD file);
 a step of controlling a bio-printing equipment for the deposition of a plurality of layers of living cells and biomaterials; and
 an optional 2D characterization step for each layer during the bio-printing step, wherein it further comprises:

a step of calculating a digital printing model according to the digital model of the product to be manufactured;

a predictive development model, as well as of the characteristics of the components to be printed (interest for customization); and the step of controlling the bio-printing equipment being carried out with the digital printing model thus calculated.

A maturation step of the printing product thus manufactured can also be provided at the end of the printing process, when preparing an in vitro model. For in situ (in vivo) printing, there is no maturation step. As for the printing of in vitro models for direct implantation, the maturation stage is partial.

The method may optionally include a step of representing and recording the sequence of tasks and operations and corresponding data, including the tasks of preparing the biological items bank, CAD, printing and maturation) that allows the history of each printing operation to be traced.

Preferably, the bio-printing method also includes a 3D characterization step of the bio-printed product during its maturation for in vitro models.

The 2D and 3D characterization steps can cover several types of shapes such as the use of topographic, tomographic, spectroscopic (Raman, Rayleigh, IR, etc.), bio-chemical analysis means, etc. They will preferably be based on 2D and 3D imaging techniques to analyze the tissue during and after printing. These techniques can be based on optical imaging techniques (confocal, fluorescence, OCT, Phase Imaging, SPIM, Multiphoton, etc.), acoustic, X-ray, etc.

According to a variant, the development prediction model is stored on a shared server, the equipment including means for communicating with the server to select from a digital library a stored development prediction model adapted to a target product category.

According to another variant, the development prediction model determines the offset between the theoretical biomaterial transfer position and the actual position of the biomaterial on the receiving target observed by the camera visualizing the target.

According to other variants, the method includes:
steps of transmitting the 2D and 3D characterizations acquired on an equipment to a server shared by a plurality of servers;
multi-agent processing steps on data from at least one connected equipment for the periodic recalculation of development prediction models; and
processing steps of the machine-learning type on data from at least one connected equipment for the periodic recalculation of development prediction models.

This periodic recalculation performs a continuous learning process with a permanent calculation on the data already acquired by data assimilation. Thus the predictive model uses previous learning for better predictions, such as:
processing steps of the continuous modelling type by differential equations on data from at least one connected equipment for the periodic recalculation of development prediction models; and
imaging space processing steps to determine viable and non-viable tissue boundaries in order to periodically recalculate the optimal printing space based on the viable tissue boundaries.

Advantageously, the connected equipment transmits to the connected server:

information including the digital model of a product to be manufactured, as well as 2D printing and 3D post-printing characterizations and in the maturation phase when there is one;
information on the physical conditions of the equipment (during the bio-printing and maturation steps if applicable);
information from the electronic laboratory notebook (ELN) on the preparation of the experiment, the preparation of cells, biomaterials and culture media; and
digital time-stamped information, descriptive of the target tissue and events detected during the bio-printing step and the maturation step when applicable.

According to a variant, the method according to the present disclosure includes a step of calculating a plurality of printing models and steps of evaluating the theoretical transformations of the printing models thus calculated, and selecting the printing model that minimizes the differences between the target model and the calculated mature model.

According to a variant, the step of calculating the printing model implements a convolution processing between the target model and a predictive development model while taking into account the inputs relating to the future printing (real components, machine, processes, etc.) in order to guarantee an optimal calculation of the printing model.

The present disclosure also relates to a bio-printing system comprising:
a bio-printing station equipped with:
at least one bio-printing head capable of controlling the transfer of biomaterials and/or living cells from a substrate to a target;
2D characterization means for recording data (morphological, molecular or chemical) of each layer during the bio-printing step;
at least one maturation station for the targets produced by bio-printing if the targets are intended for in vitro tests (without direct or indirect implantation);
as well as a computer controlling the bio-printing station, comprising means for defining and recording in the computer memory a target digital model representative of the three-dimensional organization of the product to be manufactured, wherein it includes a computer associated with a memory for recording a plurality of digital models predictive of the development of the products and executes a program controlling:
a step of calculating a digital printing model according to;
the target digital model of the product to be manufactured;
a predictive model of development;
the characteristics of the printed components; and
a step of controlling the bio-printing station by applying the calculated digital printing model.

Advantageously, the system includes:
a plurality of bio-printing stations, each of the bio-printing stations including means for communicating with a common server including the computer, the computer transmitting to each local computer associated with a bio-printing station the digital model to be applied by the bio-printing head according to each targeted application;
a plurality of bio-printing stations equipped with means for transmitting the 2D characterizations acquired during bio-printing to the server, as well as physical sensors for transmitting to the server time-stamped information from the bio-printing context; and a plurality of maturation stations including means for transmitting 3D images acquired during maturation to the server, as well as physical sensors for transmitting to the server time-stamped information from the maturation context when applicable. Physical sensors can also be integrated directly into the core of the printed item and can participate in the data collection described here.

According to a variant, the method includes processing steps of the continuous modelling type by differential equations on data from at least one connected equipment for the periodic recalculation of development prediction models.

According to another variant, the method includes multi-agent modelling type processing steps on data from at least one connected equipment for the periodic recalculation of development prediction models.

These development prediction models are cell type-specific models, either by multi-agent models or by continuous models.

Advantageously, the method involves processing according to a plurality of models, for example, one or more multi-agent models and one or more continuous models and taking the prediction weighted according to the veracity of the models according to the space of their viable parameters.

According to another variant, the method includes processing steps such as machine-learning modelling on data from at least one connected equipment for the periodic recalculation of development prediction models.

According to a variant, these models are integrated multi-scale models, for example, the genetic scale (cellular specification by GRN), can be used to define a space of parameters for the cellular scale (multi-agents) that can be the entry points of a continuous (tissue) model.

Advantageously, the connected equipment transmits to the connected server information including the digital model of a product to be manufactured, as well as 2D printing characterizations and 3D post-printing and maturing characterizations.

In a variant, the connected equipment transmits to the connected server information about the physical conditions of the equipment during the bio-printing and maturation steps.

Advantageously, the connected equipment transmits to the connected server digital time-stamped information, describing the target tissue, its environment (environment, environmental conditions) and events detected during the bio-printing and maturation steps.

According to a particular embodiment, the method includes a step of calculating a plurality of printing models and steps of evaluating the theoretical transformations of the printing models thus calculated and of selecting the printing model minimizing the differences between the target model and the calculated mature model.

According to a variant, the printing model calculation step implements a convolution processing between the target model and a predictive development model.

The present disclosure also relates to a bio-printing system comprising:
a bio-printing station equipped with:
at least one bio-printing head capable of controlling the transfer of biomaterials and/or living cells from a substrate to a target;
2D characterization means for recording data (morphological, molecular or chemical) of each layer during the bio-printing step;
at least one maturation station for the target items produced by bio-printing if the targets are intended for in vitro tests (without direct or indirect implantation);
as well as a computer controlling the bio-printing station, comprising means for defining and recording in the computer memory a target digital model representative of the three-dimensional organization of the product to be manufactured, wherein the computer includes a memory for recording a plurality of digital models predictive of the development of the product, and runs a program controlling:
a step of calculating a digital printing model according to;
the target digital model of the product to be manufactured;
a predictive model of development;
the characteristics of the printed components; and
a step of controlling the bio-printing station by applying the calculated digital printing model.

Advantageously, the system according to the present disclosure comprises a plurality of bio-printing stations, each of the bio-printing stations comprising means for communicating with a common server comprising the computer, the computer transmitting to a second local computer associated with a bio-printing station the digital model to be applied by the bio-printing head.

Advantageously, the system includes a plurality of bio-printing stations equipped with means for transmitting 2D characterizations acquired during bio-printing to the server, as well as physical sensors for transmitting to the server time-stamped information from the bio-printing context. Physical sensors can also be integrated directly into the core of the printed item and can participate in the data collection described here.

According to a variant, the system according to the present disclosure includes a plurality of maturation stations including means for transmitting post-printing and maturing 3D characterizations when applicable to the server, as well as physical sensors for transmitting to the server time-stamped information from the maturation context.

BRIEF DESCRIPTION OF THE DRAWINGS

Other characteristics and advantages will appear from the following description of the present disclosure, the description being given by way of example only, with reference to the appended drawings in which:

FIG. 4 is an operating diagram illustrating the various sequences of the method according to the present disclosure.

DETAILED DESCRIPTION

Figure 1:
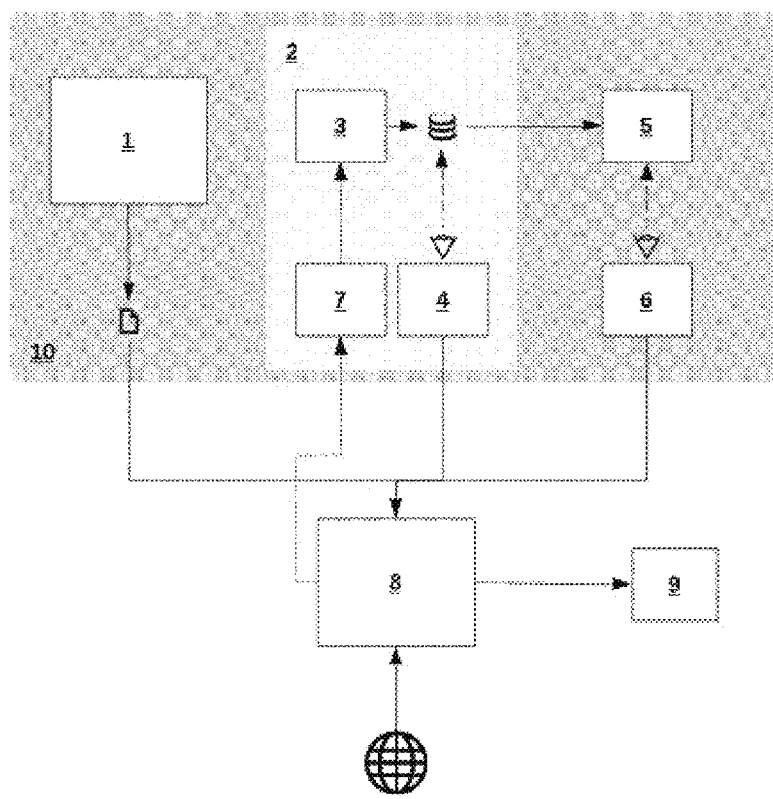
FIG. 1 is a schematic view of a system according to the present disclosure.

The precision provided by laser-assisted printing, which allows unique cells to be positioned, opens up a new and very broad field of research on cell organization within a tissue. Thanks to multiple characterization techniques, particularly of living cells, a massive database on this subject is built up over time. To be exploited, these raw data can be organized into models, i.e. abstract constructions capable of articulating the data in relation to each other. In this way it becomes possible to identify behaviors in time and space, to give an explanation (biological, mechanical, physical, etc.) about a particular organizational process or to make predictions about the actual system. In addition, some of these models can be treated in a mathematical or computerized way, thus making it possible to use the algebraic resolution capacity of mathematics or the calculation power of computers as described in the article Ballet, P., Pothet, A., Misevic, G., Jeannin-Girardon, A., Fronville, A., & Rodin, V. (2013), A multi-agent approach for simulation in cell biolog., The discreet and continuous life, 155-194.

The present disclosure is implemented on a system consisting mainly of the following workstations:

a computer workstation (1) for the definition of a target model corresponding to the configuration of a living tissue expected after the maturation or implantation of the model obtained by bio-printing;

a bio-printing instrument (2) comprising:

one or more bio-printing heads (3) for transferring biomaterials or living cells from a substrate to a target;

a camera (4) observing the target to produce 2D images during the bio-printing phase, in particular, for the verification of layer-by-layer transfers, the 2D characterization being able to take many forms other than imaging;

a local computer (7) controlling the printing bio-printing head (3); and a maturation station (5) receiving the target at the end of the bio-printing phase and setting maturation parameters for the tissue thus produced. This maturation station (5) also includes a 3D imaging system (6) for the periodic acquisition of a 3D image of the maturing tissue. Characterization can be performed with solutions other than imaging. Moreover, this maturation step only takes place when the tissue is intended for in vitro tests.

The above-mentioned technical means constitute a first local subset (10). In this description, the described bio-printing station uses laser-assisted transfer technology, but this example of technology is not limiting, and other bio-printing technologies may be employed in embodiments of the present disclosure.

A central computer (8) receives the data from the computer workstation (1), the camera (4) of the bio-printing station, the 3D imaging system (6) of the maturing station and transmitting to the local computer (7) the digital control files of the bio-printing head (3). Of course, the local computer (7) and the central computer (8) can be combined into a single piece of equipment. The central computer (8) can also be remote, in the form of a server, and, in particular, for sharing this resource with a plurality of bio-printing and maturation stations.

The central computer (8) is associated with a memory database (9) for the recording of digital development models.

The central computer (8) also receives data from internal sources, for example, biological data from the laboratory notebook on the origin of biomaterials or cells to be transferred, or from external sources, for example, bibliographic data or files corresponding to development models developed by third parties. Biological data are commonly referred to as "omes" or "omics" and include, for example, genomic, protein, or metabolic data or transcriptomic data (from RNA sequencing).

The central computer (8) is associated with a data management station (e.g., database) with a storage structure.

The bio-printing station is, for example, of the AFA-LIFT (trade name) type or equipment described in Patent Application Publication No. WO2016097619, allowing the transfer of particles or cells in a unitary manner, but the present disclosure is not limited to a particular bio-printing technology.

Figure 2:
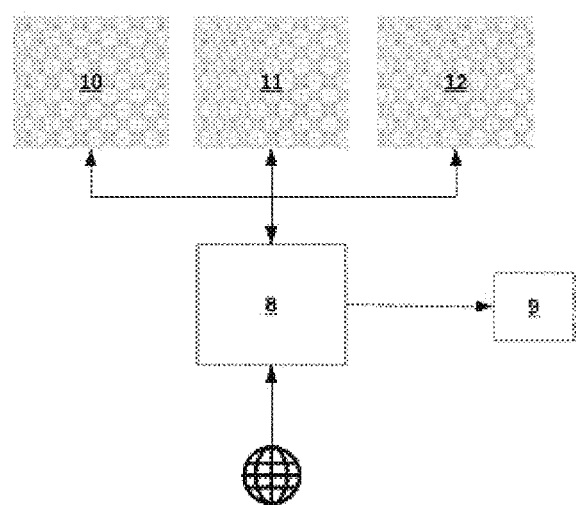
FIG. 2 shows a schematic view of a system according to a variant combining a plurality of devices with a shared server.

FIG. 2 represents a schematic view of a variant wherein several devices (10-12) are connected to a central computer (8), and process data from the various connected devices to create digital development models calculated based on data from all devices (10-12), and not just from one specific device.

Figure 3:
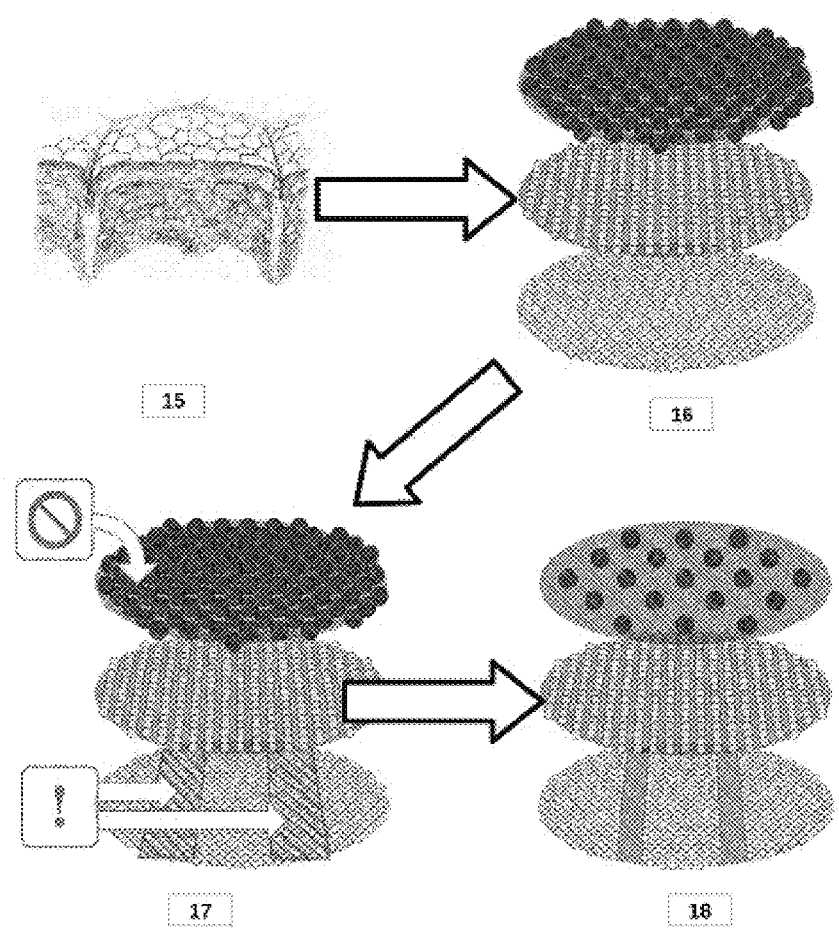
FIG. 3 is a schematic view of a bio-printing method according to the present disclosure.

FIG. 3 shows a schematic view of the processing implemented by embodiments of the present disclosure.

The first step is to determine an expected tissue type, for example, in the form of a metamodel (15) representative of the expected final item. This metamodel determines, in particular, the three-dimensional location of biomaterials or living cells in the target item and takes into account the nature of the components, in particular, their level of cellular differentiation in the final item.

For example, if the expected tissue is skin, the metamodel will determine the composition of the constituent layers including:

a layer of fibroblasts (cells) and collagen and proteoglycans (biomaterials) constituting the extracellular matrix, this layer corresponding to the dermis;

a layer of keratinocytes (cells) corresponding to the epidermis; and an intermediate zone corresponding to the dermo-epidermal junction.

The first processing consists in constructing a digital representation of this metamodel, constituting the target digital model (16). This target digital model is translated, for example, into a digital matrix of the type [ID±, C±, X±, Y±, Z±] where:

ID± corresponds to an identifier of each item;

C± corresponds to the characteristics of the item ID± (e.g., the nature of the object, its maturity, its size, etc.); and X±, Y±, Z± correspond to the spatial coordinates of the item in the target.

This target digital model (16) can be developed item by item by the user, or by a computer tool generating this target digital model (16) from a collection of metamodels whose configurable digital target model is precalculated and stored in a computer memory.

The user can thus modify given data of the pre-calculated digital model, for example, specific characteristics of certain items, or a modification of the item density or the global size of the model (addition of material, removal of material, selection of layers not to be printed, etc.) or by merging or combining several pre-calculated models.

In the state of the art, this target digital model (16) is used to control the bio-printing head. This solution generally does not allow the tissue to be manufactured in conformity with the expected configuration. Indeed, the cells and biomaterials transferred according to the implantation determined by this target digital model (16) evolve, and the tissue is transformed between the bio-printing step and the end of the maturation or implantation of the bio-printed tissue.

The purpose of the present disclosure is to solve this problem by using a solution consisting in not using this target digital model (16) to control the bio-printing station, but in calculating a digital printing model (17) by a digital processing applied to the target digital model (16).

This processing consists of a matrix development, taking into account:
a) the target digital model (16) referred to above;
b) a digital model of the development (18) of the elements contained in the target digital model (16); and
c) the characteristics of the components to be printed.

The digital development model includes:

digital representations of the endogenous behavior of each of the biomaterials or living cells likely to be transferred, recorded as digital files in the database (9) or in log files. These digital representations consist, for example, of a function defining the temporal development of a characteristic C of a given element (size, mortality, differentiation, division, etc.) or the spatial development due to displacement, migration or proliferation, or the automatic creation of new elements derived from the transferred element; and optionally digital representations of the exogenous behavior of an element according to its environment (presence within a given radius of one or more elements of the same type, presence within a given radius of one or more elements of a different type, physico-chemical conditions observed during maturation, etc.).

These digital representations can be deterministic in nature, through generic knowledge of the biological behavior of one or more elements, or empirical, through behavioral observation and learning.

In both cases, the digital representation will technically result in a digital matrix allowing digital processing for the development of a target digital model (16) into a digital printing model (17).

Digital processing consists, for example, of matrix development processing or iterative multi-agent processing, or "life game" processing (cellular automaton).

For example, U.S. Pat. Nos. 7,000,093 and 5,432,718 describe a cellular automaton adapted to the development of digital development models.

This printing model (17) is the model driving the bio-printing station.

The bio-printing step is performed with equipment ensuring the transfer of biomaterial(s) and/or living cells according to a sequence defined from the digital printing model (17) and an optimization of the temporal sequence of shots in order to minimize printing time in order to ensure maximum cellular viability, which amounts to minimizing the relative displacements of the printing head with respect to the substrate containing the transferable elements and/or optimizing the displacements according to the development of the target.

The printing station includes a target observation camera (4), which periodically acquires the 2D image of the target. This image is transmitted to the local computer (7) for evaluating the conformity of the transfer with the digital printing model (17) and possibly recalculating the sequence of future laser shots to correct the abnormalities observed. The 2D characterization can take other forms than imaging such as biochemical analysis, spectroscopic analysis, etc. The correction of the printing can also involve sucking out areas where there have been too many printed elements.

These 2D images are also transmitted to the central computer (8) for recording in connection with the current bio-printing information. This recorded information includes:

Data from the computer workstation (1) and, in particular:
the metamodel (15), when applicable;
the target digital model (16);
references to the development models (18) used for the calculation of the digital printing model (17);
the digital printing model (17);
the characteristics of the components to be printed; and
the data from the electronic laboratory notebook on printing conditions.

The data from the bio-printing station, including:
2D time-stamped images acquired by the camera (4) and other data characterizing the printed layers during the bio-printing phase;
the information relating to the sequence of laser shots, in the case of laser-assisted bio-printing; and
the time-stamped information from physico-chemical sensors such as temperature, humidity, etc. and any sensors present in the printed item; and the data from the maturation station (5) and, in particular:
the time-stamped 3D images acquired by the imaging system (6) during the bio-printing phase and other characterizations of the printed item (biochemical, spectroscopic, etc.); and
the time-stamped information from physico-chemical sensors in the maturation station, such as temperature, humidity, etc., and any sensors present in the printed item.

This data is processed by the central computer (8) to identify the differences between the 3D image transmitted by the imaging system (6) during maturation and the digital printing model (17) at the end of maturation. This processing makes it possible to verify the development of the tissue since its bio-printing phase, and to calculate the differences between the 3D image transmitted by the imaging system (6) and the digital printing model (17), which must be less than a threshold value.

This deviation calculation is carried out, for example, by an Euclidean distance calculation or a Mahalanobis distance calculation based on the determination of a correlation indicator (calculated from covariance matrices) between the digital printing model (17) and the 3D image transmitted by the imaging system (6). Alternatively, the deviation calculation is performed by a data clustering method.

These data are also stored in a memory of the central computer (8), to allow improvement processing of the digital development models (18) stored in the database (9).

Processing to recalculate development models (18) are automatic or statistical learning methods ("machine learning") known in the state of the art.

These processings are periodically applied to a collection of data corresponding to a common metamodel (15) and resulting from a plurality of bio-printings performed.

If the system includes a server common to several bio-printing and maturation platforms (10 to 12), it increases data collection and therefore the robustness of this recalculation process of the development models (18).

According to a particular embodiment, the common server is distributed or duplicated over several servers to benefit from redundancy, with a NoSQL database management system.

In this case, it is advantageous that the library of development models (18) is not stored in a local memory of the local computer (7), but in a memory common to all platforms (10 to 12) connected to a shared server (8), which can also act as a centralized computer with high data processing capacities.

According to a non-limiting example embodiment, for each cell type a digital representation of the class type (in object-oriented language) is recorded with the following functions:

attributes such as position in a space of reference (e.g., Cartesian coordinates of the geometric center of cell i at a given time, of x±, y±, z± and t type), cell type, cell age, etc., the data present in the electronic laboratory notebook; and methods of development of each cell type (evolve, migrate, divide, etc.) by means of a volumetric representation in the form of a cloud of mass "dots" in two types of interaction:

internal dots of N size classes in rigid contact with damping but without adhesion or friction, with a compression interaction model; and the membrane dots, all of the same size, are linked by visco-elastic cable elements represented by one or more digital parameters (tensors) for interaction with other neighboring cells. This assembly representing the cell membrane encapsulates the internal dots with which they are in rigid contact.

This complex digital modelling of cells in 3D over time represents fundamental development mechanisms such as growth, quiescence, differentiation, apoptosis and cell division.

The growth of a cell can be modelled by periodically recalculating the digital parameters of each cell as follows:

every n seconds, a new internal dot is added to the center of cell i. This integer n± is a parameter that then defines the growth rate of the cell (Vcrs_cell) and is empirically determined as a function of the overall dynamics of the system;

if n is too small, the growth rate of the cells is too high, the internal dots of the cell do not have time to organize themselves, so the cell does not have a stable shape; and if n is too large, the cell grows slowly and the simulation time increases. In addition, the size of the new internal dot added to the cell is determined by the number of dots already present. Thus, a cell has the same number of internal dots of each size to the nearest point in order to maintain a regular grain size and/or cell shape (elongation).

The development of tissue resulting from accretionary development can be modelled using the following parameters:

the growth rate of the cell $V_{crs\ cell}$;

the speed of arrival of the cells by cell division $V_{accretion}$; and the growth rate of the sphere $V_{crs\ sphere}$.

All these parameters define a speed of tissue development.

The dynamic calculation of the temporal development of a tissue is carried out by a computer program taking into account the temporal development of each cell and the neighboring intracellular interactivities.

The development stages modelled by digital parameters are as follows:

determination of dividing cells;
beginning of the division: creation of the actin elements;
development of the division: reduction of the actin elements;
end of division: the mother cell gives two daughter cells;
development of "cadherin" type elements that directly influence cell adhesion;
determination of the cells to undergo apoptosis; and
development of apoptosis: removal of dots and/or cells.

At each passage in the "tissue evolution" loop, not all operations are taken into account for each cell and only the adapted methods are performed. For example, a cell that is not differentiated cannot enter quiescence and a cell in division cannot enter apoptosis.

The temporal development of each cell takes into account boundary conditions and time-dependent development assumptions. This calculation is performed iteratively to determine at each step the new positions and speeds for each dot. The structural development of the system, i.e., the addition or deletion of dots or elements, according to the data obtained from mechanical calculations and following the laws of development that govern the model, is carried out according to the development model of division and apoptosis.

Cells and tissue are constructed according to data recorded in a file defining the initial configuration (positioning of dots, characteristics of dots and elements, etc.) and parameters of digital morphogenesis: type of scenario (tissue formed by accretion or proliferation), division, etc. Then, regularly during the simulation, the membranes of each cell are updated (elongation, reduction, removal and addition of membrane cables in accordance with the rules for membrane development), regardless of the type of scenario.

Then, depending on the initialized tissue development choice, the "non-proliferative tissue" or "proliferative tissue" algorithm is executed. The cells are thus modified according to the previously defined laws (type of division, apoptosis, growth, etc.). Similarly, the modelling takes into account the development of the extra-cellular matrix (density, rigidity, molecular signaling, etc.).

The time step chosen is, for example, 0.5 second to recalculate the development of the tissue between two iterations.

For example, the digital parameters and development functions are as follows:

| | |
|---|---|
| growth rate of the cell: Vcrs cell | adding a node every 100 time steps |
| accretion rate of the cells: Vaccretion | addition of cells every 50 time steps |
| growth rate of the sphere: Vcrs_sphere | 5% increase in the surface area of the sphere every 50 time steps |
| apoptosis rate: Vapop | deletion of 5 dots every 100 time steps |
| renewal of "cadherin" cables | "updated every n_cad time step: n_cad = 50 |
| minimum distance to create a cadherin element | minimum distance D_cad between two dots: D_cad = 13 m |

This modelling allows an intermediate digital model (32) to be determined, whose development will lead to a target tissue or product (30) corresponding to a digital file (40).

The determination can be made by testing different intermediate digital models (32) and estimating the corresponding target digital files (40), to select the digital file (40) closest to the expected tissue.

FIG. 4 illustrates schematically the principle implemented by embodiments of the present disclosure.

The first step is to define the three-dimensional structure of the tissue to be made, in the form of an electronic laboratory notebook or CAD file. This file defines the target structure with the theoretical implantation of cells and particles in a three-dimensional network resulting in a digital file (40) that specifies the target product (30). The characterization of the 3D structure can be multi-modal, multi-scale and automated.

In addition, an evolution or development model (41) describing the developments of the different cells and particles leads to a file or series of digital files defining the development model (31). The development model takes into account endogenous developments, such as ageing, size evolution, differentiation, disappearance or duplication, as a function of time and other environmental parameters such as temperature, or the development of the physico-chemical composition of the substrate, for an isolated particle or cell. It also takes into account exogenous parameters such as the presence, nature and distance of other particles or cells that exert mechanical forces and emit paracrine signals.

These two series of files (40 and 41) are processed to calculate a reference model (42) by applying an intermediate digital model (32), consisting in determining an initial three-dimensional structure whose development, according to the development model (41), gives a result consistent with the target product (30), by an inverse estimation function or empirically, by determining a reference model assumption, applying the development model and comparing the result with the target product (30), recursively to minimize the differences between the result of applying the development model to the reference model (42) and the target product (30).

This reference model (42) will drive the bio-printing process that will produce a tissue whose construction is characterized layer by layer to provide intermediate printing data (33) subject to verification (43) and validation or correction steps.

According to a variant, the item is then matured. Its development is also analyzed by measurement and control methods, in particular, imaging to provide a digital representation (44) of the tissue at different stages of development.

According to other variants, the item is implanted directly or very quickly after its manufacture, referred to as partial maturation.

According to another ultimate variant, the item is directly printed in situ, notably in vivo on the animal or patient. There is no maturation in this case. It is done directly at the implantation site.

The invention claimed is:
1. A bio-printing method, comprising:
   a step of preparing a target digital model representative of a three-dimensional organization of tissue to be manufactured;
   a step of calculating a digital printing model according to the target digital model of a product to be manufactured, and a predictive development model, as well as characteristics of components to be printed; and
   a step of controlling a bio-printing equipment for deposition of a plurality of layers of living cells and bio-materials carried out according to the digital printing model thus calculated.
2. The method of claim 1, further comprising a 2D characterization step of each of the plurality of layers during the bio-printing step.
3. The method of claim 1, further comprising a step of maturing a printed item.
4. The method of claim 1, further comprising a step of 3D characterization of a bio-printed product immediately after the bio-printing.
5. The method of claim 1, further comprising a step of 3D characterization of a bio-printed product during its maturation.
6. The method of claim 1, wherein the predictive development model is stored on a shared server, the bio-printing equipment including means for communicating with the server to select from a digital library a recorded predictive development model adapted to a target product category.
7. The method of claim 1, further comprising transmitting a 2D or 3D characterization acquired on the bio-printing equipment to a server shared between a plurality of servers.
8. The method of claim 1, further comprising performing multi-agent processing steps on data from the bio-printing equipment for a periodic recalculation of predictive development models.
9. The method of claim 1, further comprising applying machine learning processing steps on data from the bio-printing equipment for a periodic recalculation of predictive development models.
10. The method of claim 1, further comprising applying continuous modelling processing steps using differential equations on data from the bio-printing equipment for a periodic recalculation of the predictive development model.
11. The method of claim 6, wherein the bio-printing equipment transmits to a connected server information including the digital model of a product to be manufactured, 2D printing images, and 3D maturing images.
12. The method of claim 6, wherein the bio-printing equipment transmits to the server information relating to the physical conditions of the bio-printing equipment during the bio-printing step.
13. The method of claim 6, wherein the bio-printing equipment transmits to the server digital time-stamped information, descriptive of the tissue to be manufactured, the environment surrounding the tissue, and events detected during the bio-printing step.
14. The method of claim 6, wherein the bio-printing equipment transmits to the server time-stamped digital information from sensors present inside the tissue.
15. The method of claim 1, further comprising calculating a plurality of printing models, and evaluating theoretical developments of the printing models thus calculated, and selecting a printing model having minimal differences between the target digital model and the calculated mature printing model.
16. The method of claim 1, wherein the step of calculating the digital printing model implements a convolution processing between the target digital model and a predictive development model.
17. A bio-printing system, comprising:
   a bio-printing station equipped with:
      at least one bio-printing head capable of controlling a transfer of biomaterials and/or living cells to a target;
      2D characterization means for recording data of each layer during a bio-printing step; and
      a computer controlling the bio-printing station, comprising means for defining and recording in memory of the computer a target digital model representative of a three-dimensional organization of a product to be manufactured; and
   a computer associated with a memory for recording a plurality of digital predictive development models, and storing a program that, when executed by the computer, controls:
      a step of calculating a digital printing model calculated according to:
         the target digital model of the product to be manufactured;
         a predictive development model and characteristics of components to be printed; and
         a step of controlling the bio-printing station by application of the calculated digital printing model.
18. The system of claim 17, further comprising at least one maturation station for the target.

19. The system of claim 17, further comprising a plurality of bio-printing stations, each of the bio-printing stations comprising means for communicating with a common server comprising the computer associated with the memory for recording the plurality of digital predictive development models, the common server transmitting to each computer controlling the respective bio-printing station the target digital model to be applied by the bio-printing head according to the target.

20. The system of claim 19, wherein each of the plurality of bio-printing stations is equipped with means for transmitting 2D data acquired during bio-printing to the server, as well as physical sensors for transmitting to the server time-stamped information from a bio-printing context.

21. The system of claim 19, further comprising a plurality of maturation stations including means for transmitting 3D data acquired during maturation to the server, as well as physical sensors for transmitting to the server time-stamped information from a maturation context.

\* \* \* \* \*